United States Patent [19]

Azadian et al.

[11] 4,242,335
[45] Dec. 30, 1980

[54] NOVEL 17α-ARYL-STEROIDS

[75] Inventors: Geneviéve Azadian, Paris; Daniel Philibert, La Varenne Saint-Hilaire; André Pierdet, Noisy-le-Sec, all of France

[73] Assignee: Roussel Uclaf, Paris, France

[21] Appl. No.: 955,403

[22] Filed: Oct. 27, 1978

[30] Foreign Application Priority Data

Nov. 8, 1977 [FR] France .................. 77 33557

[51] Int. Cl.³ .............................................. C07J 1/00
[52] U.S. Cl. ................................ 424/243; 260/397.4; 260/397.45; 260/239.55 C
[58] Field of Search ........................ 260/397.4, 397.45; 424/241

[56] References Cited

U.S. PATENT DOCUMENTS

| | | | |
|---|---|---|---|
| 2,774,777 | 12/1956 | Djerassi et al. | 260/397.4 |
| 3,069,421 | 12/1962 | Nomine et al. | 260/239.55 C |
| 3,086,027 | 4/1963 | Perelman et al. | 260/397.3 |
| 3,176,010 | 3/1965 | Cooley et al. | 260/397.4 |
| 3,178,456 | 4/1965 | Wettstein et al. | 260/239.55 C |
| 3,257,278 | 6/1966 | Nomine et al. | 260/239.55 C |

Primary Examiner—Elbert L. Roberts
Attorney, Agent, or Firm—Hammond & Littell, Weissenberger and Muserlian

[57] ABSTRACT

Novel 17α-aryl-steroids of the formula

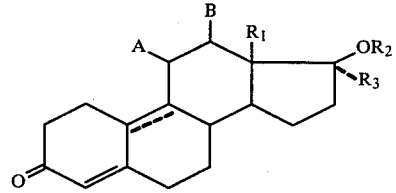

wherein $R_1$ is alkyl of 1 to 3 carbon atoms, $R_2$ is selected from the group consisting of hydrogen, alkyl of 1 to 12 carbon atoms and acyl of an organic carboxylic acid of 1 to 18 carbon atoms, $R_3$ is aryl of 6 to 12 carbon atoms optionally substituted with at least one substituent selected from the group consisting of —OH, halogen, alkoxy and alkyl of 1 to 4 carbon atoms and —CF$_3$, the dotted line in the B ring indicating an optional double bond in the 9(10)-position, and A and B are hydrogen and when there is a double bond in the 9(10)-position, A and B form a double bond in the 11(12) position or B is hydrogen and A is an 11β-hydroxy having progestomimetic activity activity without androgenic activity and a process for their preparation and novel intermediates produced therein.

32 Claims, No Drawings

NOVEL 17α-ARYL-STEROIDS

OBJECTS OF THE INVENTION

It is an object of the invention to prepare the novel 17α-aryl-steroids of formula I and to a novel process for their preparation and novel intermediates.

It is another object of the invention to provide novel progestomimetic compositions and to a novel method inducing progestomimetic activity in warm-blooded animals without androgenic activity.

These and other objects and advantages of the invention will become obvious from the following detailed description.

THE INVENTION

The novel 17α-aryl steroids of the invention have the formula

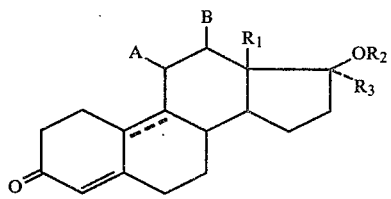

wherein $R_1$ is alkyl of 1 to 3 carbon atoms, $R_2$ is selected from the group consisting of hydrogen, alkyl of 1 to 12 carbon atoms and acyl of an organic carboxylic acid of 1 to 18 carbon atoms, $R_3$ is aryl of 6 to 12 carbon atoms optionally substituted with at least one substituent selected from the group consisting of —OH, halogen, alkoxy and alkyl of 1 to 4 carbon atoms and —CF$_3$, the dotted line in the B ring indicating an optional double bond in the 9(10)-position, and A and B are hydrogen and when there is a double bond in the 9(10)-position, A and B form a double bond in the 11(12)-position or B is hydrogen and A is an 11β-hydroxy. Preferably $R_1$ is methyl or ethyl.

Examples of $R_2$ are alkyl such as methyl, ethyl, propyl, isopropyl, butyl, isobutyl, tert.-butyl, n-pentyl, n-hexyl, 2-methyl-pentyl, 2,3-dimethyl butyl, n-butyl, 2-methyl-hexyl, 2,2-dimethyl pentyl, 3,3-dimethyl-pentyl, 3-ethyl-pentyl, n-octyl, 2,2-dimethyl-hexyl, 3,3-dimethyl-hexyl, 3-methyl-3-ethyl-pentyl, nonyl, 2,4-dimethyl-heptyl and n-decyl.

Examples of organic carboxylic acids of 1 to 18 carbon atoms when $R_2$ is acyl are saturated or unsaturated aliphatic or cycloaliphatic carboxylic acids, especially alkanoic acids such as formic acid, acetic acid, propionic acid, butyric acid, isobutyric acid or undecylic acid; haloalkanoic acids such as chloroacetic acid; cycloalkylcarboxylic acids such as cyclopropylcarboxylic acid, cyclopentylcarboxylic acid and cyclohexylcarboxylic acid; cycloalkylalkanoic acids such as cyclopentylacetic acid, cyclohexylacetic acid, cyclopentylpropionic acid and cyclohexylpropionic acid; benzoic acid, phenylalkanoic acids such as phenylpropionic acid; and amino acids such as diethylaminoacetic acid or aspartic acid.

$R_3$ is preferably phenyl but may be naphthyl, both optionally substituted with at least one member of the group consisting of halogens like fluorine, chlorine, alkoxy of 1 to 4 carbon atoms such as methoxy or ethoxy, alkyl of 1 to 4 carbon atoms such as methyl or ethyl or —CF$_3$.

Among the preferred compounds of formula I are those wherein the B ring is saturated and A and B are hydrogen, those wherein the B ring contains a double bond in the 9(10)-position and those having a double bond both in the 9(10) and 11(12)-positions. Preferably $R_1$ is methyl, $R_3$ is phenyl and $R_2$ is hydrogen. Preferred compounds of formula I are 17α-phenyl-Δ$^4$-estrene-17β-ol-3-one, 17α-phenyl-Δ$^{4,9}$-estradiene-17β-ol-3-one and 17α-phenyl-Δ$^{4,9,11}$-estratriene-17β-ol-3-one.

The novel process of the invention for the preparation of the compounds of formula I comprises reacting a compound of the formula

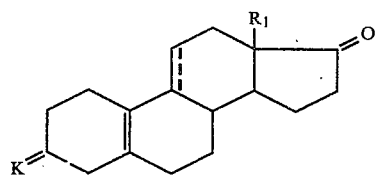

wherein K is a ketal, $R_1$ is alkyl of 1 to 3 carbon atoms and the dotted line is an optional double bond in the 9(11)-position with a compound of the formula R$_3$Li wherein R$_3$ has the above definition, reacting the resulting product and a hydrolysis agent to obtain a compound of the formula

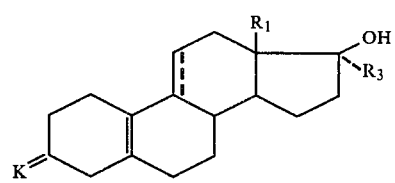

reacting the latter, if desired, with an etherification agent to obtain a compound of the formula

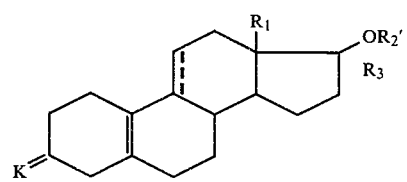

wherein $R_2'$ is selected from the group consisting of hydrogen and alkyl of 1 to 12 carbon atoms and when the C ring is saturated, reacting the latter with an acid agent able to free the ketone function to obtain a compound of the formula

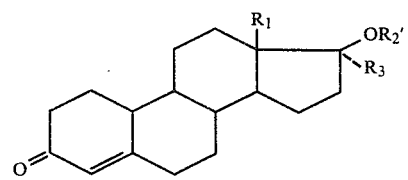

with when the C ring contains a double bond in the 9(11)-position, either reacting the compound of formula III with an agent able to hydrolyze the ketal group and isomerize the $\Delta^{5(10),9(11)}$-system to $\Delta^{4(5),9(10)}$-double bond system to obtain a compound of the formula

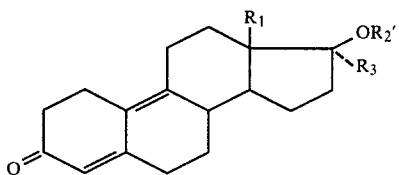

or reacting the compound of formula III with an agent able to hydrolyze the ketal group without isomerizing the double bond system to obtain a compound of the formula

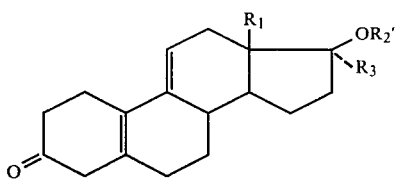

and reacting the latter with a substituted p-benzoquinone to obtain a compound of the formula

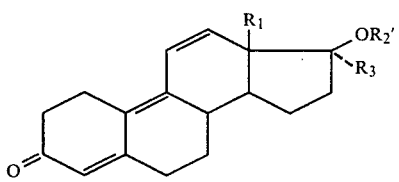

or reacting the compound of formula IV with a hydroperoxidation agent and then a reducing agent to obtain a compound of the formula

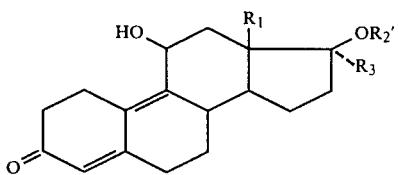

which when R$_2'$ is hydrogen, may be reacted with an etherification agent or an esterification agent to obtain the corresponding compounds of formula I wherein R$_2$ is alkyl or acyl.

In the compounds of formula II, K is preferably a cyclic alkyl ketal of 2 to 4 carbon atoms, especially ethylene ketal or propylene ketal but may also be a dialkyl ketal such as dimethyl ketal or diethylketal. The reaction of the compound of formula II is preferably effected in ethyl ether or tetrahydrofuran or a mixture thereof.

When the C ring of the compound of formula III is saturated, the preferred agent to free the ketone is acetic acid and the etherification agent is preferably an alkyl halide such as alkyl chloride or a sulfonate or an alkyl arylsulfonate. The acid hydrolysis agent capable of hydrolyzing the ketal and isomerizing the double bond system is preferably a commercial sulfonic resin supported by polystyrene or a copolymer of styrene-divinylbenzene but also useful are inorganic acids such as hydrochloric acid or a sulfonic acid in a lower alkanol or perchloric acid in acetic acid or a sulfonic acid such as p-toluene sulfonic acid.

The acid hydrolysis agent capable of hydrolyzing the ketal without isomerizing the double bond system is preferably aqueous acetic acid. The substituted p-benzoquinone is preferably 2,3-dichloro-5,6-dicyano-p-benzoquinone, 2,3-dibromo-5,6-dicyano-p-benzoquinone, 2,3,5,6-tetrachloro-p-benzoquinone, 2,3-dicyano-5-chloro-p-benzoquinone or 2,3-dicyano-p-benzoquinone and the said reaction is preferably effected in an organic solvent such as dioxane, methylene chloride, dichloroethane, benzene, toluene, ethyl acetate or propyl acetate.

The hydroperoxidation agent is preferably oxygen in the presence of an amine such as triethylamine or pyridine. The reducing agent to reduce the hydroperoxide is preferably a trialkyl phosphite such as trimethyl phosphite. The esterification agent is preferably an anhydride or acid chloride of the carboxylic acid and the reaction is effected in the presence of a basic catalyst such as pyridine or N,N-dimethylamino-pyridine.

In a preferred mode of the process of the invention, K is ethylene ketal and when the C ring is saturated, the agent to free the ketone is acetic acid, the hydrolysis agent which will also isomerize the double bond system is a sulfonic acid resin on a polystyrene or styrene-divinylbenzene copolymer support, the hydrolysis agent which will not isomerize the double bond system is aqueous acetic acid and the substituted p-benzoquinone is 2,3-dichloro-5,6-dicyano-p-benzoquinone.

The novel intermediates of the invention are those of formula III. The compounds of formula II which are the starting materials may be made by the process of U.S. Pat. No. 2,806,030 of French Pat. No. 1,336,083.

The novel progestomimetic compositions of the invention are comprised of a progestomimetically effective amount of at least one compound of formula I and an inert pharmaceutical carrier or excipient. The compositions may be in the form of tablets, dragees, cachets, capsules, granules, emulsions, syrups, suppositories, injectable solutions or suspensions, pomades, creams, gels and aerosol preparations.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants and emulsifiers or preservatives.

The compositions possess a good progestomimetic activity without androgenic activity and are useful for the treatment of pathological disorders due to insufficiency of progesterone such as amenorrhea, metrorrhagia, irregular cycles, hypermenorrhea, oligomenorrhea or dysmenorrhea as well as for the treatment of tumors of breast and of uterus without worry of secondary effects which occur with the use of adrogens. They can also be used in contraception alone in continuous administration or associated with estrogens in intermittent administration. The preferred compositions contain 17α-phenyl-$\Delta^4$-estrene-17β-ol-3-one or 17α-phenyl-$\Delta^{4,9,11}$-estratriene-17β-ol-3-one.

The novel method of the invention of inducing progestomimetic activity in warm-blooded animals, including humans, without androgenic activity comprising administering to warm-blooded animals a progestomimetically effective amount of at least one compound of formula I. The compounds may be administered orally, rectally, parenterally or topically to the skin or mucus. The usual daily effective dose is 1γ to 1 mg/kg depending upon the specific compound and the method of administration.

In the following examples there are described several preferred embodiments to illustrate the invention. However, it should be understood that the invention is not intended to be limited to the specific embodiments.

EXAMPLE 1

17α-phenyl-Δ$^4$-estrene-17β-ol-3-one (Product A)

STEP A:
3,3-ethylenedioxy-17α-phenyl-Δ$^{5(10)}$-estrene-17β-ol 100 ml of a solution of 1.15 N phenyllithium in ether were added to a solution of 10 g of 3,3-ethylenedioxy-Δ$^{5(10)}$-estrene-17-one (prepared by process of U.S. Pat. No. 2,806,030) in 20 ml of tetrahydrofuran and the mixture was stirred under an inert atmosphere for 5 hours. The resulting suspension was poured into 1.5 liters of an aqueous solution saturated with ammonium chloride and the mixture was extracted with ether. The ether extracts were washed with water, dried over sodium sulfate and were evaporated to dryness under reduced pressure. The resin residue was added to 10 ml of isopropyl ether and the mixture was iced overnight. The mixture was vacuum filtered and the recovered product was dried to obtain 5 g of 3,3-ethylenedioxy-17α-phenyl-Δ$^{5(10)}$-estrene-17β-ol with a melting point of 168° C.

STEP B: 17α-phenyl-Δ$^4$-estrene-17β-ol-3-one

A suspension of 5 g of the product of Step A in 100 ml of 60% aqueous acetic acid was heated with stirring at 60° C. for one hour and the mixture was then cooled and poured into 1.5 liters of distilled water. The mixture was extracted with methylene chloride and the organic extracts were washed with aqueous sodium bicarbonate until the wash water was neutral and then with water, dried and evaporated to dryness under reduced pressure. The white resin was chromatographed over silica gel and was eluted with an 8-2 benzene-ethyl acetate mixture to obtain 2.5 g of 17α-phenyl-Δ$^4$-estrene-17β-ol-3-one with a melting point of 172° C. and an Rf=0.48.

Analysis: $C_{24}H_{30}O_2$; molecular weight=350.48. Calculated: %C 82.24, %H 8.63. Found: %C 82.1, %H 8.6.

EXAMPLE 2

17α-phenyl-Δ$^{4,9}$-estradiene-17β-ol-3-one (Product B)

STEP A:
3,3-ethylenedioxy-17α-phenyl-Δ$^{5(10),9(11)}$-estra-diene-17β-ol 9.1 ml of a solution of 1.05 M of phenyllithium in ethyl ether were added to a mixture of 1 g of 3,3-ethylenedioxy-Δ$^{5(10),9(11)}$-estradiene-17-one in 10 ml of tetrahydrofuran cooled to −50° C. and the mixture was stirred at −50° C. under an inert atmosphere for 30 minutes. Then, 9.6 ml of a solution of one mole of water per liter of tetrahydrofuran was added to the mixture followed by stirring at −50° C. for 10 minutes, addition of another 9.1 ml of the 1.05 M phenyllithium solution and stirring at −50° C. for one hour. The said procedure was repeated a second time and then 10 ml of an aqueous solution saturated with ammonium chloride were added thereto. The organic phase was washed with water, dried over sodium sulfate, filtered and evaporated to dryness to obtain 1.49 g of raw product. The latter was chromatographed over silica gel and was eluted with a 95-5 benzeneethyl acetate mixture to obtain 0.60 g of 3,3-ethylenedioxy-17α-phenyl-Δ$^{5(10),9(11)}$-estradiene-17β-ol with an Rf=0.41.

STEP B: 17α-phenyl-Δ$^{4,9}$-estradiene-17β-ol-3-one 13 g of Redex CF resin were added at 20° C. to a mixture of 6.5 g of the product of Step A in 130 ml of ethanol and the mixture was stirred overnight under an inert atmosphere at 20° C. The mixture was filtered and the resin was rinsed with ethanol. The alcoholic filtrate was concentrated, was diluted with ethyl acetate and the mixture was washed with an aqueous saturated sodium bicarbonate solution and then with water. The organic phase was dried over sodium sulfate and was evaporated to dryness to obtain 5.670 g of raw product which was chromatographed over silica gel. Elution with an 8-2 benzene-ethyl acetate mixture yielded 4.43 g of 17α-phenyl-Δ$^{4,9}$-estradiene-17β-ol-3-one with a specific rotation of $[\alpha]_D^{20}=-199°\pm4°$ (c=0.5% in $CHCl_3$).

Analysis: $C_{24}H_{28}O_2$; molecular weight=348.46. Calculated: %C 82.72, %H 8.09. Found: %C 82.1, %H 8.1.

EXAMPLE 3

17α-phenyl-Δ$^{4,9,11}$-estratriene-17β-ol-3-one (Product C)

STEP A:
17α-phenyl-Δ$^{5(10),9(11)}$-estradiene-17β-ol-3-one

A solution of 9.1 g of the product of Step A of Example 2 in 273 ml of acetic acid containing 5% of water was stirred under an inert atmosphere at room temperature for 30 minutes and then 51 ml of water were added thereto. The mixture was stirred for 19 hours in the dark at room temperature and was then poured into 2 liters of aqueous sodium bicarbonate solution. The mixture was vacuum filtered and the recovered precipitate was washed with water and then with an aqueous saturated sodium bicarbonate solution and was dried to obtain 6.751 g of 17α-phenyl-Δ$^{5(10),9(11)}$-estradiene-17β-ol-3-one which was used as is for the next step.

STEP B: 17α-phenyl-Δ$^{4,9,11}$-estratriene-17β-ol-3-one 8.850 g of dichlorodicyanobenzoquinone were added to a solution of 6.750 g of the product of Step A in 675 ml of benzene and the mixture was stirred in the dark under an inert atmosphere for 6 hours. The mixture was vacuum filtered and the recovered precipitate was washed with benzene. The filtrate was washed with 0.2 N sodium thiosulfate solution and then with water, dried over sodium sulfate and evaporated to dryness to obtain 7.20 g of raw product. The latter was chromatographed over silica gel and was eluted with an 8-2 benzene-ethyl acetate mixture to obtain 5.317 g of 17α-phenyl-Δ$^{4,9,11}$-estratriene-17β-ol-3-one with a specific rotation of $[\alpha]_D^{20}=+105°$ (c=0.5% in $CHCl_3$).

Analysis: $C_{24}H_{26}O_2$; molecular weight=346.54. Calculated: %C 83.17, %H 7.56. Found: %C 83.3, %H 7.7.

PHARMACOLOGICAL STUDY

A. Progestomimetic Activity

The progestomimetic activity was determined by the hormonal receptor method of Raynaud et al [J. Ster. Biochem., Vol. 6 (1975), p-615–622 and Physiology and Genetics of Reproduction, part A (1975), p. 143–160]. Immature rabbits received subcutaneously 25γ of estradiol and 5 days later, the animals were sacrificed and the uterus was removed and homogenized in a buffered solution of 10 mM of tromethamine, 0.25 M of saccharose and a pH of 7.4 with hydrochloric acid. The homogenate was centrifuged at 105,000 g during one hour and the surnageant or cytosol was adjusted to a dilution of 1/50 (weight/volume). The resulting solution was incubated at 0° C. for 2 hours in tubes with the same volume of cytosol with a fixed concentration of tritiated 17,21-dimethyl-19-nor-$\Delta^{4,9}$-pregnadiene-3-20-dione (designated as tritiated Product R) in the presence or not of an increasing concentration of radioinactive 17,21-dimethyl-19-nor-$\Delta^{4,9}$-pregnadiene-3,20-dione (designated as cold product R) or progesterone or the test product. The radioactivity of the tritiated product R was determined after 2 hours by the technique of adsorption on carbon-dextran (1.25-0.625%). The curves representing the percentage of tritiated product R as a function of the log of the concentration, of cold product R, of progesterone or the test products and the $I_{50}$ straight line parallel to the axis of the abcissess and ordinates $$\frac{B}{T} = \frac{B/T\,Max. + B/T\,Min.}{2}$$

were ploted. B/T max. is the percentage of tied tritiated product R when the product is not added and B/T min. is the percentage of tied tritiated product R when the maximum amount of cold product R is added. The intersections of these $I_{50}$ straight lines and the curves permit the determination of the values: CP and CX: CP - concentration of cold progesterone which inhibits by 50% the fixation of the tritiated product R and CX - concentration of test product which inhibits by 50% the fixation of the tritiated product R. The relative affinity of the test product (ARL) was determined by the formula $$ARL = 100 \times \frac{CP}{CX}$$

and the results are reported in Table I.

TABLE I

| Product | ARL |
|---|---|
| Progesterone | 100 |
| ethynyl nortestosterone | 100 |
| A | 80 |
| B | 37 |
| C | 27 |

The results of Table I show that product A has an affinity for specific uterine reception of progesterone comparable to that of progesterone while products B and C have an activity about 3 times weaker than progesterone. Products A, B and C are progestomimetics.

B. Androgenic Activity

This test also used the method of Raynaud et al discussed above. The prostate was recovered from male rats castrated 24 hours earlier and was homogenized in a buffer containing 10 mM of tromethamine and 0.25 M of saccharose and sufficient hydrochloric acid for a pH of 7.4 The homogenate was centrifuged at 105,000 g for one hour and the surnageant liquid or cytosol was adjusted to a dilution of 1/5 (weight/volume). The liquid was incubated at 0° C. for 2 hours with a fixed concentration of tritiated 17α-methyl-$\Delta^{4,9,11}$-estratriene-17β-ol-3-one (tritiated product R) in the presence or absence of increasing concentration of the same cold product (designated as cold product R), testosterone or the test compound.

The radioactivity of the tied tritiated product was determined after 2 hours by absorption technique on carbondextran (1.25%–0.625%). The curves representing the percentage of tied tritiated product R as a function of the log of the concentration of the cold product R, testosterone or the test product added and the $I_{50}$ straight line parallel to the axis of the abcisses and ordinates $$\frac{B}{T} = \frac{B/T\,Max. + B/T\,Min.}{2}$$

were plotted. B/T max. is the percentage of tied tritiated product R when the product is not added and B/T min. is the percentage of tied tritiated product R when the maximum amount of cold product R is added. The intersections of these $I_{50}$ straight lines and the curves permit the determination of the values: CT-concentration of cold testosterone which inhibits by 50% the fixation of the tritiated product R and CX-concentration of test product which inhibits by 50% the fixation of tritiated product R. The relative affinity of the test product (ARL) was determined by the formula $$ARL = 100 \times \frac{CT}{CX}$$

and the results are reported in Table II.

TABLE II

| Product | ARL |
|---|---|
| Testosterone | 100 |
| ethynylnortestosterone | 42 |
| A | 0.3 |
| B | 0.2 |
| C | ≦0.1 |

The results of Table II show that products A, B and C are practically devoid of an affinity for prostatic reception of testosterone while ethynylnortestosterone has a marked affinity for prostatic reception of testosternone. Products A, B and C are devoid of adrogenic activity while ethynylnortesterone has a marked androgenic activity.

C. In vivo progestomimetic activity

The progestomimetic activity of products A, B and C were determined by the Clauberg test on immature rabbits previously sensibilized by subcutaneous administration of estradiol for 5 days at a daily dose of 5 μg. The test products were used in solution in olive oil containing 5% of benzyl alcohol and were subcutaneously administered for 5 days at different doses. The animals were killed on the 6th day and the uterus was removed to determine the proliferation of endometric lacework which is characteristic of progestomimetic activity. The results were compared with ethynylnortesterone administered in the same method in the same solvent. The results were expressed in MacPhail units in Table III.

TABLE III

| Product | Dose | MacPhail Units |
|---|---|---|
| A | 100 γ | 2 |
|   | 500 γ | 2.7 |

TABLE III-continued

| Product | Dose | MacPhail Units |
|---|---|---|
|  | 2500 γ | 3 |
|  | 200 γ | 1 |
| B | 1 mg | 2.8 |
|  | 2 mg | 3.0 |
| C | 200 γ | 0.8 |
|  | 1 mg | 1.8 |
|  | 2 mg | 2.9 |
| ethynylnortestosterone | 100 γ | 1.2 |
|  | 500 γ | 1.5 |
|  | 2500 γ | 2 |

The results of Table III show that products A and B have a progestomimetic activity greater than ethynylnortestosterone while product C has about the same order of activity as ethynylnortestosterone.

Various modifications of the products and process of the invention may be made without departing from the spirit or scope thereof and it is to be understood that the invention is intended to be limited only as defined in the appended claims.

We claim:

1. A compound of the formula

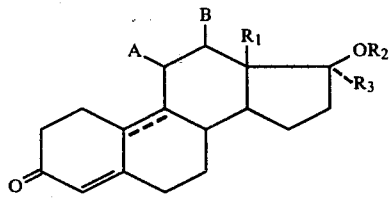

wherein $R_1$ is alkyl of 1 to 3 carbon atoms, $R_2$ is selected from the group consisting of hydrogen, alkyl of 1 to 12 carbon atoms and acyl of an organic carboxylic acid of 1 to 18 carbon atoms, $R_3$ is selected from the group consisting of phenyl and naphthyl optionally substituted with at least one substituent selected from the group consisting of —OH, halogen, alkoxy and alkyl of 1 to 4 carbon atoms and —$CF_3$, the dotted line in the B ring indicating an optional double bond in the 9(10) position, and A and B are hydrogen and when there is a double bond in the 9(10) position, A and B form a double bond in the 11(12) position or B is hydrogen and A is an 11β-hydroxy.

2. A compund of claim 1 wherein $R_1$ is methyl.

3. A compound of claims 1 or 2 wherein $R_3$ is phenyl.

4. A compound of claim 1 wherein $R_2$ is hydrogen.

5. A compound of claim 1 wherein the B ring is saturated and A and B are hydrogen.

6. A compound of claim 1 wherein the B ring is ethylenically unsaturated in the 9(10) position.

7. A compound of claim 1 wherein the B ring is ethylenically unsaturated in the 9(10)-position and the C ring is ethylenically unsaturated in the 11(12)-position.

8. A compound of claim 1 which is 17α-phenyl-Δ⁴-estrene-17β-ol-3-one.

9. A compound of claim 1 which is 17α-phenyl-$\Delta^{4,9}$-estradiene-17β-ol-3-one.

10. A compound of claim 1 which is 17α-phenyl-$\Delta^{4,9,11}$-estratriene-17β-ol-3-one.

11. A progestomimetic composition comprising a progestomimetically effective amount of at least one compound of claim 1 and an excipient.

12. A composition of claim 11 wherein $R_1$ is methyl.

13. A composition of claim 11 wherein $R_3$ is phenyl.

14. A composition of claim 11 wherein $R_2$ is hydrogen.

15. A composition of claim 11 wherein the B ring is saturated and A and B are hydrogen.

16. A composition of claim 11 wherein the B ring is ethylenically unsaturated in the 9(10)-position.

17. A composition of claim 11 wherein the B ring is ethylenically unsaturated in the 9(10)-position and the C ring is ethylenically unsaturated in the 11(12)-position.

18. A composition of claim 11 which is 17α-phenyl-Δ⁴-estrene-17β-ol-3-one.

19. A composition of claim 11 which is 17α-phenyl-$\Delta^{4,9}$-estradiene-17β-ol-3-one.

20. A composition of claim 11 which is 17α-phenyl-$\Delta^{4,9,11}$-estratriene-17β-ol-3-one.

21. A method of inducing progestomimetic activity in warm-blooded animals without androgenic activity comprising administering to warm-blooded animals a progestomimetically effective amount of at least one compound of claim 1.

22. A method of claim 21 wherein $R_1$ is methyl.

23. A method of claim 21 wherein $R_3$ is phenyl.

24. A method of claim 21 wherein $R_2$ is hydrogen.

25. A method of claim 21 wherein the B ring is saturated and A and B are hydrogen.

26. A method of claim 21 wherein the B ring is ethylenically unsaturated in the 9(10)-position.

27. A method of claim 21 wherein the B ring is ethylenically unsaturated in the 9(10)-position and the C ring is ethylenically unsaturated in the 11(12)-position.

28. A method of claim 21 which is 17α-phenyl-Δ⁴-estrene-17β-ol-3-one.

29. A method of claim 21 which is 17α-phenyl-$\Delta^{4,9}$-estradiene-17β-ol-3-one.

30. A method of claim 21 which is 17α-phenyl-$\Delta^{4,9,11}$-estratriene-17β-ol-3-one.

31. A compound of the formula

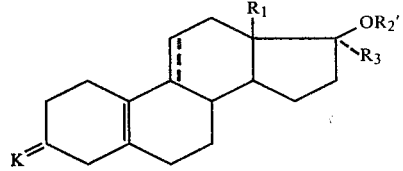

wherein K is a ketal selected from the group consisting of dimethylketal, diethylketal and alkylenedioxy of 2 to 4 carbon atoms, $R_1$ is alkyl of 1 to 3 carbon atoms, $R_2'$ is selected from the group consisting of hydrogen and alkyl of 1 to 12 carbon atoms, $R_3$ is selected from the group consisting of phenyl and naphthyl optionally substituted with at least one member selected from the group consisting of —OH, halogen, alkyl and alkoxy of 1 to 4 carbon atoms and —$CF_3$ and the dotted line indicates an optional double bond.

32. A process for the preparation of a compound of claim 1 comprising reacting a compound of the formula

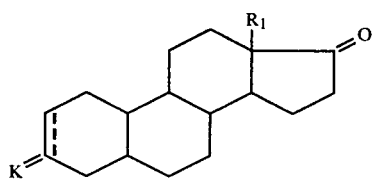

wherein K is a ketal selected from the group consisting of dimethylketal, diethylketal and alkylenedioxy of 2 to 4 carbon atoms, $R_1$ is alkyl of 1 to 3 carbon atoms and the dotted line is an optional double bond in the 9(11)-position with a compound of the formula $R_3Li$ wherein $R_3$ has the above definition, reacting the resulting product with a hydrolysis agent to obtain a compound of the formula

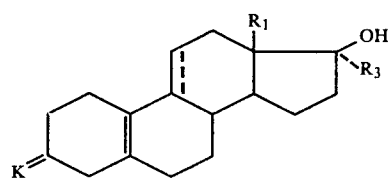

reacting the latter, if desired, with an etherification agent selected from the group consisting of alkyl halides, alkyl sulfonates and alkyl arylsulfonates to obtain a compound of the formula

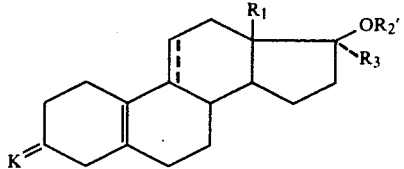

and reacting the latter with a substituted p-benzoquinone to obtain a compound of the formula

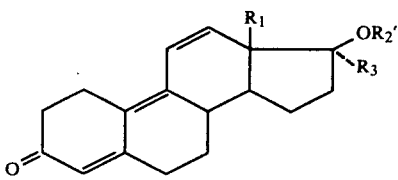

or reacting the compound of formula IV with oxygen in the presence of an amine and then a trialkylphosphate to obtain a compound of the formula

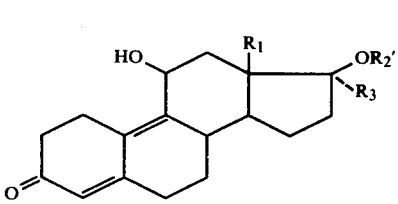

which when $R_2'$ is hydrogen, may be reacted with an etherification agent or acid chloride or anhydride to obtain the corresponding compounds of formula I wherein $R_2$ is alkyl or acyl.

* * * * *